United States Patent
Maisel et al.

(10) Patent No.: US 10,485,757 B2
(45) Date of Patent: *Nov. 26, 2019

(54) HYPOTONIC HYDROGEL FORMULATIONS FOR ENHANCED TRANSPORT OF ACTIVE AGENTS AT MUCOSAL SURFACES

(71) Applicant: The Johns Hopkins University, Baltimore, MD (US)

(72) Inventors: Katharina Maisel, Troy, MI (US); Laura Ensign, Towson, MD (US); Justin Hanes, Baltimore, MD (US); Richard Cone, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/546,772

(22) PCT Filed: Jan. 26, 2016

(86) PCT No.: PCT/US2016/014956
§ 371 (c)(1),
(2) Date: Jul. 27, 2017

(87) PCT Pub. No.: WO2016/123125
PCT Pub. Date: Aug. 4, 2016

(65) Prior Publication Data
US 2018/0021435 A1    Jan. 25, 2018

Related U.S. Application Data

(60) Provisional application No. 62/108,354, filed on Jan. 27, 2015.

(51) Int. Cl.
| | |
|---|---|
| *A61K 9/00* | (2006.01) |
| *A61K 47/10* | (2017.01) |
| *A61K 9/51* | (2006.01) |
| *A61K 31/09* | (2006.01) |
| *A61K 31/365* | (2006.01) |
| *A61K 31/352* | (2006.01) |
| *A61K 9/06* | (2006.01) |
| *A61K 31/52* | (2006.01) |
| *A61K 31/675* | (2006.01) |
| *A61K 8/90* | (2006.01) |

(52) U.S. Cl.
CPC .............. *A61K 9/0031* (2013.01); *A61K 8/90* (2013.01); *A61K 9/0034* (2013.01); *A61K 9/06* (2013.01); *A61K 9/5146* (2013.01); *A61K 9/5153* (2013.01); *A61K 31/09* (2013.01); *A61K 31/352* (2013.01); *A61K 31/365* (2013.01); *A61K 31/52* (2013.01); *A61K 31/675* (2013.01); *A61K 47/10* (2013.01)

(58) Field of Classification Search
CPC .. A61K 2300/00; A61K 31/09; A61K 31/365; A61K 47/10; A61K 31/352; A61K 31/52; A61K 31/675; A61K 9/0034; A61K 9/5146; A61K 9/5153; A61K 8/90; A61K 9/0031; A61K 9/06
See application file for complete search history.

(56) References Cited

U.S. PATENT DOCUMENTS

| | | |
|---|---|---|
| 4,997,652 A | 3/1991 | Wong |
| 5,034,506 A | 7/1991 | Summerton |
| 5,578,325 A | 11/1996 | Domb |
| 5,710,135 A | 1/1998 | Leenders |
| 5,869,130 A | 2/1999 | Ferrier |
| 5,932,462 A | 8/1999 | Harris |
| 6,007,845 A | 12/1999 | Domb |
| 6,287,588 B1 | 9/2001 | Shih |
| 6,413,539 B1 | 7/2002 | Shalaby |
| 6,495,164 B1 | 12/2002 | Ramstack |
| 6,509,323 B1 | 1/2003 | Davis |
| 6,589,549 B2 | 7/2003 | Shih |
| 6,706,289 B2 | 3/2004 | Lewis |
| 8,354,476 B2 | 1/2013 | Hanes |
| 8,409,607 B2 | 4/2013 | Hughes |
| 8,465,778 B2 | 6/2013 | Hughes |
| 8,481,069 B2 | 7/2013 | Hughes |

(Continued)

FOREIGN PATENT DOCUMENTS

| | | |
|---|---|---|
| CA | 1072413 | 2/1980 |
| WO | 9207866 | 5/1992 |

(Continued)

OTHER PUBLICATIONS

Astete and Sabliov, "Synthesis and characterization of PLGA nanoparticles", J Biomater Sci Polymer Ed., 17:247-89 (2006).

(Continued)

*Primary Examiner* — Mark V Stevens
(74) *Attorney, Agent, or Firm* — Pabst Patent Group LLP

(57) ABSTRACT

Hypotonic formulations of hydrogel forming polymers, preferably poloxamers, have been developed for enhanced delivery through mucosa of therapeutic, diagnostic, prophylactic or other agents, to epithelial tissues, especially those having a mucosal coating. The polymers are administered at a concentration above, at or less than their critical gelling concentration (CGC) under isotonic conditions. The hypotonicity of the formulation is adjusted so that the polymer gels at the lower concentration. A Poloxamer gel administered into the vagina or colorectum at its CGC will form a "plug" of gel in the lumen.

20 Claims, 9 Drawing Sheets

(56) References Cited

U.S. PATENT DOCUMENTS

| | | | |
|---|---|---|---|
| 8,512,738 | B2 | 8/2013 | Edelman |
| 8,628,801 | B2 | 1/2014 | Garreta |
| 8,632,809 | B2 | 1/2014 | Asgharian |
| 8,663,674 | B2 | 3/2014 | Wen |
| 8,911,768 | B2 | 12/2014 | Whitcup |
| 2003/0068277 | A1 | 4/2003 | Vanbever |
| 2004/0234611 | A1 | 11/2004 | Ahlheim |
| 2005/0009910 | A1 | 1/2005 | Hughes |
| 2007/0071756 | A1 | 3/2007 | Peyman |
| 2007/0149593 | A1 | 6/2007 | Ghosh |
| 2007/0219122 | A1 | 9/2007 | Glazer |
| 2007/0231360 | A1 | 10/2007 | Peyman |
| 2008/0070920 | A1 | 3/2008 | Guo |
| 2008/0086199 | A1 | 4/2008 | Dave |
| 2008/0166414 | A1 | 7/2008 | Hanes |
| 2008/0305172 | A1 | 12/2008 | Ahlheim |
| 2009/0196844 | A1* | 8/2009 | Choi ............... A61K 31/765 424/78.3 |
| 2009/0203709 | A1 | 8/2009 | Steinberg |
| 2010/0227905 | A1 | 9/2010 | Kabra |
| 2011/0262406 | A1 | 10/2011 | Campo |
| 2012/0052041 | A1 | 3/2012 | Basu |
| 2012/0157499 | A1 | 6/2012 | Hughes |
| 2012/0269894 | A1 | 10/2012 | Ahlheim |
| 2013/0071349 | A1 | 3/2013 | Robinson |
| 2013/0122064 | A1 | 5/2013 | Ahlheim |
| 2013/0316001 | A1 | 11/2013 | Popov |
| 2013/0316006 | A1 | 11/2013 | Popov |
| 2013/0316009 | A1 | 11/2013 | Popov |
| 2014/0031408 | A1 | 1/2014 | Edelman |
| 2014/0107025 | A1 | 4/2014 | Wirostko |
| 2014/0163080 | A1* | 6/2014 | Horn ................ A61K 9/0048 514/396 |
| 2014/0178475 | A1 | 6/2014 | Figueiredo |
| 2014/0248358 | A1 | 9/2014 | Figueiredo |
| 2014/0249158 | A1 | 9/2014 | Figueiredo |
| 2014/0271903 | A1 | 9/2014 | Sutariya |
| 2014/0276482 | A1 | 9/2014 | Astafieva |
| 2014/0294986 | A1 | 10/2014 | Liu |

FOREIGN PATENT DOCUMENTS

| | | | |
|---|---|---|---|
| WO | 94027578 | 12/1994 | |
| WO | 2006063249 | 6/2006 | |
| WO | 2007016380 | 2/2007 | |
| WO | 2007084418 | 7/2007 | |
| WO | 2008061536 | 5/2008 | |
| WO | WO-2009055312 A1 * | 4/2009 | ............ A61L 15/60 |
| WO | 2010040188 | 4/2010 | |
| WO | 2010132664 | 11/2010 | |
| WO | 2013110027 | 7/2013 | |
| WO | 2013166408 | 11/2013 | |
| WO | 2013166436 | 11/2013 | |
| WO | 2014039186 | 3/2014 | |
| WO | 2014047439 | 3/2014 | |
| WO | WO-2014039185 A1 * | 3/2014 | ........... A61K 9/0036 |

OTHER PUBLICATIONS

Bertschinger, et al., "Disassembly of polyethylenimine-DNA particles in vitro: implications for polyethylenimine-mediated DNA delivery", J Control Release, 116:96-104 (2006).

Bonacucina, et al., Thermosensitive Self-Assembling Block Copolymers as Drug Delivery Systems. Polymers, 3(2):779-811 (2011).

Chen, et al., "pH and temperature dual-sensitive liposome gel based on novel cleavable mPEG-Hz-CHEMS polymeric vaginal delivery system", Int J Nanomedicine, 7:2621-30 (2012).

Clark and Friend, "Pharmacokinetics and Topical Vaginal Effects of Two Tenofovir Gels in Rabbits", AIDS Res Hum Retroviruses, 28(11):1458-66 (2012).

Cone, et al., "Barrier properties of mucus", Adv Drug Delivery Rev., 61:75-85 (2009).

Cu, et al., "In vivo distribution of surface-modified PLGA nanoparticles following intravaginal delivery", J Cont. Release, 156(2):257-64 (2011).

Das Neves and Bahia, "Gels as vaginal drug delivery systems", Int J Pharm., 318(1-2):1-14 (2006).

Deosarkar, et al.., "Polymeric particles conjugated with a ligand to VCAM-1 exhibit selective, avid, and focal adhesion to sites of atherosclerosis", Biotech. Bioeng., 101(2):400-7 (2008).

Desi, et al., "Localization of Herpes Simplex Virus Type 1 UL37 in the Golgi Complex Requires UL36 but Not Capsid Structures", J Virology, 82(22):11354-61 (2008).

Dong, et al., "Vascular cell-adhesion molecule-1 plays a central role in he proangiogenic effects of oxidative stress", PNAS, 108(35):14614-9 (2011).

Dumortier, et al., "A review of poloxamer 407 pharmaceutical and pharmacological characteristics", Pharm Res., 23(12):2709-28 (2006).

Dunmire and Katz, "Alteration of human sperm kinematics in cervical mucus due to nonoxynol-9", Contraception, 55:209-17 (1997).

Duvall, et al., "Phase 2: a dose-escalation study of OncoGel (ReGel/paclitaxel), a controlled-releaseformulation of paclitaxel, as adjunctive local therapy to external-beam radiation in patients with inoperableesophageal cancer", Anticancer Drugs, 20(2):89-95 (2009).

Ensign, et al., "Ex vivo characterization of particle transport in mucus secretions coating freshly excised mucosal tissues", Mol Pharm, 10(6):2176-82 (2013).

Ensign, et al., "Mucus Penetrating Nanoparticles: Biophysical Tool and Method of Drug and Gene Delivery", Adv Mater. 24(28):3887-94 (2012b).

Ensign, et al., "Mucus-penetrating nanoparticles for vaginal drug delivery protect against herpes simplex virus", Science Translational Med., 4:138ra179 (2012).

Eyles, et al., "The transfer of polystyrene microspheres from the gastrointestinal tract to the circulation after oral administration in the rat", J Pharm. Pharmacol., 47:561-5 (1995).

Fuchs, et al., "Hyperosmolar sexual lubricant causes epithelial damage in the distal colon: potential implication for HIV transmission", J Infect Dis 195:703-710 (2007).

Garripelli, et al., "Drug Release from a pH-Sensitive Multiblock Co-Polymer Thermogel", J Biomater Sci Polym Ed, 23(12):1505-19 (2011).

Giovagnoli, et al, "Formulation and release behavior of doxycycline-alginate hydrogel microparticles embedded into pluronic F127 thermogels as a potential new vehicle for doxycycline intradermal sustained delivery", AAPS PharmSciTech, 11(1):212-20 (2010).

Gref, et al., "'Stealth' corona-core nanoparticles surface modified by polyethylene glycol (PEG): influences of the corona (PEG chain length and surface density) and of the core composition on phagocytic uptake and plasma protein adsorption", Colloids Surf Biointerfaces, 18:301-13 (2000).

International Search Report for corresponding PCT application PCT/US2017/014956 dated Apr. 22, 2016.

Jain, "The manufacturing techniques of various drug loaded biodegradable poly(lactide-co-glycolide) (PLGA) devices", Biomaterials, 21(23):2475-90 (2000).

Kim, et al., "A thermosensitive vaginal gel formulation with HPgammaCD for the pH-dependent release andsolubilzation of amphotericin B", Eur J Pharm Sci, 2010. 41(2):399-406 (2010).

Lacey, et al., "Unacceptable side-effects associated with a hyperosmolar vaginal microbicide in a phase 1 trial", Int J STD AIDS, 21:714-7 (2007).

Lai, et al., "Rapid transport of large polymeric nanoparticles in fresh undiluted human mucus", PNAS, 104(5)1482-7 (2007).

Lai., "Mucus-penetrating nanoparticles for drug and gene delivery to mucosal tissues", Adv Drug Deliv Rev., 61(2): 158-171 (2009).

Lemoine, et al., "Mechanism of efficient transfection of the nasal airway epithelium by hypotonic shock", Gene Ther., 12(16):1275-85 (2005).

Lennemas, "Does fluid flow across the intestinal mucosa affect quantitative oral drug absorption? Is it time for a reevaluation?", Pharm Res., 12:1573-82 (1995).

(56) References Cited

OTHER PUBLICATIONS

Li, et al., "A long-acting formulation of a polypeptide drug exenatide in treatment of diabetes using an injectable block copolymer hydrogel", Biomaterials, 34(11):2834-42 (2013).

Li, et al., "Microencapsulation by solvent evaporation: state of the art for process engineering approaches", Int. J. Pharm., 363(1-2):26-39 (2008).

Loh, et al., "Sustained delivery of paclitaxel using thermogelling poly(PEG/PPG/PCL urethane)s for enhanced toxicity against cancer cells", J Biomed Mater Res A., 100(10): 2686-94 (2012).

Miyazaki, et al., "Thermo-sensitive sol-gel transition of Pluronic F-127", Yakuzaigaku, 51:36-43 (1991).

Moench, et al., "Microbicide excipients can greatly increase susceptibility to genital herpes transmission in the mouse", BMC Infect Dis., 10:331 (2010).

Mundargi, et al., "Nano/micro technologies for delivering macromolecular therapeutics using poly(D,L-lactide-co-glycolide) and its derivatives", J. Control. Release, 125(3):193-209 (2008).

Nance, et al.,"A dense poly(ethylene glycol) coating improves penetration of large polymeric nanoparticles within brain tissue", Sci Transl Med., 4(149):149ral119 (2012).

Ndesendo. et al., "A Review of Current Intravaginal Drug Delivery Approaches Employed for the Prophylaxis of HIV/AIDS and Prevention of Sexually Transmitted Infections", AAPS Pharm Sci Tech, 9(2)505-20 (2008).

Noach, et al., "Effect of anisotonic conditions on the transport of hydrophilic model compounds across monolayers of human colonic cell lines", J Pharmacol Exp Ther., 270:1373-80 (1994).

Owen, et al., "Factors influencing nonoxynol-9 permeation and bioactivity in cervical mucus", J Control Release, 60:23-34 (1999).

Pandit and Wang, "Salt effects on the diffusion and release rate of propranolol from poloxamer 407 gels", Intl J Pharma., 167(1-2):183-9 (1998).

Park, et al., "Biodegradable thermogels", Acc Chem Res, 45(3):424-33 (2012).

Pihl, et al., Comparative study of the effect of luminal hypotonicity on mucosal permeability in rat upper gastrointestinal tract, Acta Physiol., 193:67-78 (2008).

Rajapaksa, et al., "Intranasal M cell uptake of nanoparticles is independently influenced by targeting ligands and buffer ionic strength", J Biol Chem., 285:23739-46 (2010).

Robinson, et al., "Isotretinoin for low-grade cervical dysplasia in human immunodeficiency virus-infected women", Obstet Gynecol, 99:777-84 (2002).

Rudolph, et al., "Aerosolized nanogram quantities of plasmid DNA mediate highly efficient gene delivery to mouse airway epithelium", Mol Ther., 12:493-501 (2005).

Segarra, et al., "Bridging the Gap between Preclinical and Clinical Microbicide Trials: Blind Evaluation of Candidate Gels in Murine Models of Efficacy and Safety", Plos One, 6(11):E27675 (2011).

Sheng, et al., "In vitro macrophage uptake and in vivo biodistribution of PLA-PEG nanoparticles loaded with hemoglobin as blood substitutes: effect of PEG content", J Mater Sci Mater Med., 20(9):1881-91 (2009).

Sonis, et al., "Perspectives on Cancer Therapy-Induced Mucosal Injury", Mucositis: Perspectives and Clinical Practice Guidelines, CANCER, Supp1100(9):1995-2025 (2004).

Thigpen, et al., "The role of chemotherapy in the management of carcinoma of the cervix", Cancer J. 9:245-432 (2003).

Veronese, et al., "PEG-doxorubicin conjugates: influence of polymer structure on drug release, in vitro cytotoxicity, biodistribution, and antitumor activity", Bioconjig Chem.,16(4):775-84 (2005).

Wang, et al., "Addressing the PEG mucoadhesivity paradox to engineer nanoparticles that "slip" through the human mucus barrier", Angew Chem Int Ed Engl., 47:9726-9 (2008).

Wang, et al., "Development of in situ gelling and bio adhesive 5-Fluorourocil enema", PLoS One, 2013. 8(8): p. e71037 (2013).

Yeon, et al., "3D culture of adipose-tissue-derived stem cells mainly leads to chondrogenesis in poly(ethylene glycol)-poly(L-alanine) dblock copolymer thermogel", Biomacromolecules, 14(9):3256-66 (2013).

Yokoyama, et al., "Characterization and anticancer activity of the micelle-forming polymeric anticancer drug adriamycin-conjugated poly(ethylene glycol)-poly(aspartic acid) block copolymer", Cancer Res., 50:1693-1700 (1990).

Yu, et al., "In vitro and in vivo evaluation of a once-weekly formulation of an antidiabetic peptide drug exenatide in an injectable thermogel", J Pharm Sci, 102(11):4140-9 (2013).

Zeitlin, et al., "Leakage of three commercial vaginal gels in women", Contraception, 68:139-55 (2003).

\* cited by examiner

HYPOTONIC HYDROGEL FORMULATIONS FOR ENHANCED TRANSPORT OF ACTIVE AGENTS AT MUCOSAL SURFACES

CROSS REFERENCE TO RELATED APPLICATIONS

This application is a 371 application of PCT/US2016/014956, filed Jan. 26, 2016, which claims priority under 35 U.S.C. 119 to U.S. Ser. No. 62/108,354 "Hypotonic Hydrogel Formulations for Enhanced Transport of Active Agents at Mucosal Surfaces" filed Jan. 27, 2015 by Katharina Maisel, Laura Ensign, Justin Hanes, and Richard Cone, the disclosures of which are hereby incorporated herein by reference in their entirety.

STATEMENT REGARDING FEDERALLY SPONSORED RESEARCH OR DEVELOPMENT

This invention was made with government support under Grant No. 5R21AI079740 and Grant No. 5R21AI094519 awarded by the National Institutes of Health. The government has certain rights in the invention.

FIELD OF THE INVENTION

This invention is generally in the field of formulations for enhanced drug delivery, in particular drug delivery at mucosal surfaces.

BACKGROUND OF THE INVENTION

The mucosa is the inner layer of any epithelially-lined hollow organ (e.g., mouth, gut, uterus, vagina, colon, anal canal, trachea, lungs, bladder, etc.). The mucosa consists of the epithelium itself and also the supporting loose connective tissue, called lamina propria, immediately beneath the epithelium. Deeper connective tissue which supports the mucosa is called the submucosa. In the GI tract (but not in other tubular organs), there is a thin layer of smooth muscle, the muscularis mucosae, at the boundary between mucosa and submucosa.

The mucosal surfaces of the body are particularly vulnerable to infection. They are thin and permeable barriers to the interior of the body because of their physiological activities in gas exchange (the lungs), food absorption (the gut), sensory activities (eyes, nose, mouth, and throat), and reproduction (uterus and vagina). The necessity for permeability of the surface lining these sites creates obvious vulnerability to infection and it is not surprising that the vast majority of infectious agents invade the human body through these routes.

Mucosal barrier injuries, such as oral and gastrointestinal mucositis, are a common complication following cytoreductive cancer therapy and radiotherapy (Sonis et al., *Cancer Supplement*, 100(9):1995-2023, 2004).

Capsid viruses can diffuse through mucus as rapidly as through water and thereby penetrate to the epithelium even though they have to diffuse 'upstream' through mucus that is being continuously secreted. These viruses are smaller than the mucus mesh spacing, and have surfaces that do not stick to mucus (Cone R. A., *Adv. Drug Deliv Rev*, 61(2):75-85, 2009). For example, women are disproportionately infected with HIV, partly owing to a lack of female-controlled prevention methods (Ndesendo et al., *AAPS PharmSciTech*, 9:505-520, 2008). An easily administered, discreet, and effective method for protecting women against vaginal HIV transmission could prevent millions of infections worldwide. However, vaginal folds, or "rugae", that accommodate expansion during intercourse and child birth, are typically collapsed by intra-abdominal pressure, making the surfaces of these folds less accessible to drugs and drug carriers (Alexander et al., *Sex Transm Dis*, 29:655-664, 2004). Poor distribution into the vaginal folds, even after simulated intercourse, has been cited as a critical factor for failure to protect susceptible vaginal surfaces from infection. Distribution over the entire susceptible target surface has been proven to be important for preventing and treating infections. Additionally, to increase user acceptability, drug delivered to the vagina should be retained in the vaginal tract at effective concentrations over extended periods of time.

Achieving sustained local drug concentrations is challenging because the vaginal epithelium is highly permeable to small molecules and also because soluble drug dosage forms (gels, creams) can be expelled by intra-abdominal pressure and ambulation. Lastly, drug delivery methods must be safe and non-toxic to the vaginal epithelium. Improvements in the distribution, retention, and safety profile of vaginal dosage forms may lead to a substantial increase in efficacy and decrease in the side effects caused by largely ineffective systemic treatments for cervicovaginal infections and diseases (Thigpen T. *Cancer J.* 9:245-432, 2003; Robinson et al., *Obstet Gynecol*, 99:777-784, 2002).

Sustained drug delivery to the mucosal surfaces of the body has potential for improving the treatment and prevention of many diseases, including sexually transmitted infections, inflammatory bowel disease, lung inflammation, and degenerative eye conditions to name only a few. Achieving sustained prophylactic or therapeutic drug concentrations using traditional soluble dosage forms remains challenging due to degradation, rapid shedding, and rapid systemic absorption of drug. There is an urgent need for compositions for delivery to mucosal surfaces that provide a physical barrier to pathogen entry. Also, there is an unmet need for compositions for mucosal delivery that offer retention and sustained release of prophylactic, therapeutic or diagnostic agents at mucosal surfaces.

Therefore, it is an object of the invention to provide improved compositions for delivery of active agents with greater efficacy and safety to mucosal surfaces that act as barriers to pathogen transport into the mucosa.

It is a further object of the present invention to provide improved compositions for delivery to mucosal surfaces that allow retention and sustained release of prophylactic, therapeutic or diagnostic agents at mucosal surfaces.

It is still a further object of the present invention to provide methods of making the improved compositions for delivery to mucosal surfaces.

SUMMARY OF THE INVENTION

Hypotonic formulations of hydrogel forming polymers, preferably poloxamers, have been developed for enhanced delivery of therapeutic, diagnostic, prophylactic or other agents, to epithelial tissues, especially those having a mucosal coating. The polymers are administered in a hypotonic solution at a concentration less than their normal critical gelling concentration (CGC). Typically, a Poloxamer gel administered into the vagina or colorectum at its CGC will form a "plug" of gel in the lumen. In contrast, fluid from a hypotonically-administered Poloxamer solution below the CGC will be absorbed by the epithelial surface, drawing the Poloxamer into the mucus layers and up against the epithelium where it then becomes concentrated enough to gel, thereby enhancing and facilitating delivery of agents to the epithelial cells. As the Poloxamer is concentrated at the tissue/mucosal interface, it mixes with mucus and gels up against the epithelial surface. The endogenous mucin glycopolymers affect the gelling properties of the hypotonic gelling agents, including the concentration of gelling agent needed to gel and the pore structure of the resulting gel/mucin mixture. The hypotonic gelling vehicles coat the epithelium, including the folds, after vaginal and colorectal application. This can be used as a barrier layer to protect the underlying mucosa or decrease penetration into the mucosa or as a depo for delivery of agent in the hydrogel.

The examples demonstrate longer vaginal retention of model drug administered in a hypotonic gelling agent compared to a bolus of gel formed in the middle of the vaginal lumen, as would be the case for a gelling agent administered at the CGC.

As also demonstrated by the examples, the concentration of the polymer and the presence of additional components such as the endogenous mucins affect coverage and rate and degree of gelling. 18% F127 gel mixed with purified pig gastric mucins (1%) or human cervicovaginal mucus (1:1 ratio) does not trap virus-sized (~100 nm) nanoparticles (polyethylene glycol coated polystyrene nanoparticles, PSPEG) as effectively as 18% F127 gel alone. In contrast, 24% F98 gel more effectively trapped PSPEG particles when mixed with mucins or human cervicovaginal mucus. However, in vivo viral trapping with hypotonic gelling agents was more effective at trapping viruses, including human immunodeficiency virus (HIV, ~120 nm) and herpes simplex virus (HSV, ~180 nm). Administration of 18% F98, having a CGC of 24%, results in effective trapping of subsequently administered HIV in the vagina. Similarly, 10% and 15% F127, having a CGC of 18%, were also effective in decreasing the MSD of HIV, indicating trapping. Additionally, both 15% F127 and 18% F98 reduced the diffusion of subsequently administered HSV in mouse vaginal mucus. The distribution of the individual virus MSD at a time scale of 1 s illustrated that the trapping (shift to the left) of the viruses was more uniform in the gel formed by the hypotonic 18% F98 vehicle compared to 15% F127. In additional tests of viral trapping by hypotonic gelling agents in the colorectum, it was found that 12% F98 (CGC 24%) did not effectively trap PSPEG nanoparticles administered 30 mins. after the gelling vehicle, though 18% F98 was effective at trapping PSPEG nanoparticles in the mouse colorectum. Importantly, these examples illustrate differences in the gels that form when the hypotonic gelling agents are administered to different mucosal surfaces, and in this case, mix with vaginal mucus compared to colorectal mucus prior to gelling.

These studies demonstrate the advantages of these hypotonic polymeric gel formulations for drug delivery, especially via hydrogel depos or barrier coatings on mucosal epithelia.

DETAILED DESCRIPTION OF THE INVENTION

I. Definitions

Figure 1:
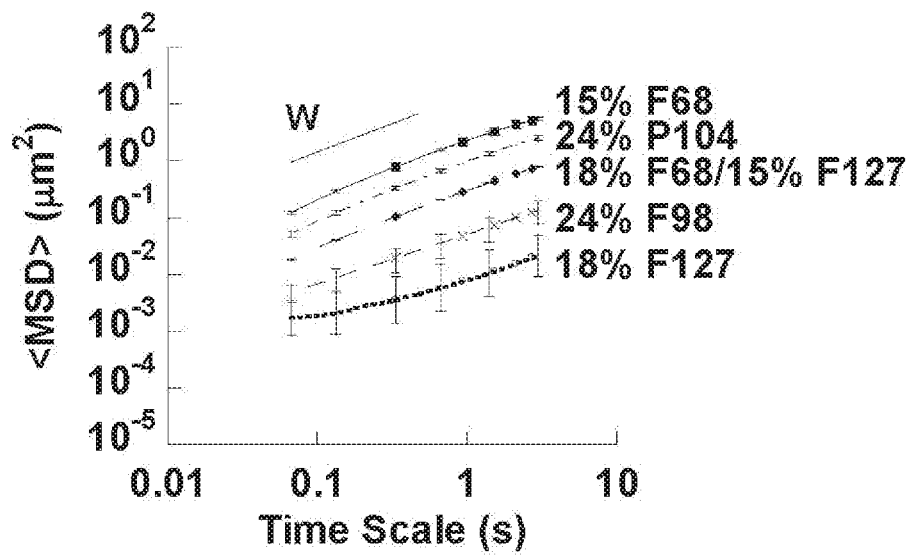
FIG. 1 is a line graph showing transport properties at 37° C. of 100 nm PSPEG nanoparticles in various thermogelling Poloxamers, nonionic triblock copolymers composed of a central hydrophobic chain of polyoxypropylene (poly(propylene oxide)) flanked by two hydrophilic chains of polyoxyethylene (poly(ethylene oxide)). Poloxamers are also known by the trade name PLURONICs®). Ensemble averaged mean-squared displacement (<MSD>, $\mu m^2$) as a function of time scale (s) for 100 nm nanoparticles in 15% F68, 24% P104, 18% F68 with 15% F127, 24% F98, or 18% F127 is presented. W represents the theoretical diffusion rate of the nanoparticles in water.
Figures 2A, 2B, 2C, 2D, 2E:
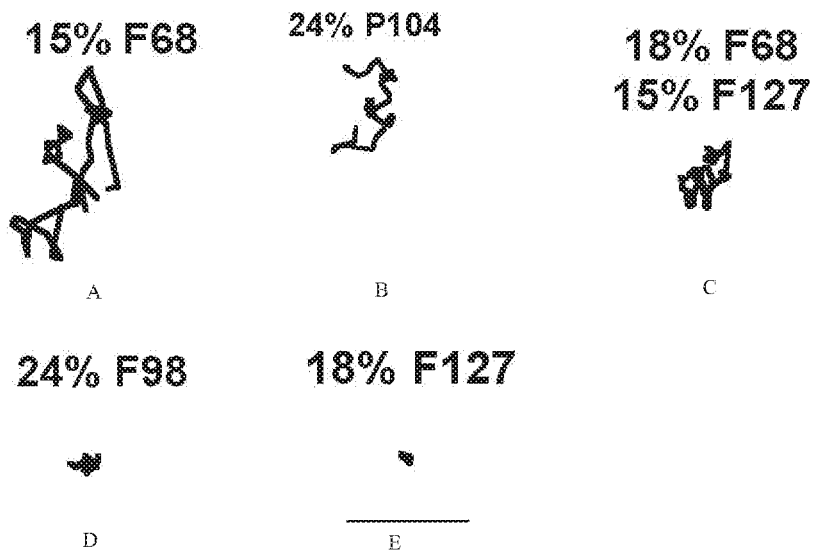
FIGS. 2A-2E are representative trajectories (3 s of motion) of 100 nm PSPEG nanoparticles in the various fluids/gels listed above at 37° C. More restricted trajectories indicate nanoparticle trapping in a gel matrix, whereas free diffusion if indicative of nanoparticles diffusing in a viscous fluid. Data is representative of n≥3 samples.

As generally used herein "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Biocompatible" and "biologically compatible", as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory, immune or toxic response when administered to an individual.

The terms "gel" and "hydrogel", as used interchangeably herein, refers to a swollen, water-containing network of finely-dispersed polymer chains that are water-insoluble, where the polymeric molecules are in the external or dispersion phase and water (or an aqueous solution) forms the internal or dispersed phase. The chains can be chemically crosslinked (chemical gels) or physically crosslinked (physical gels). Chemical gels possess polymer chains that are connected through covalent bonds, whereas physical gels have polymer chains linked by non-covalent bonds or cohesion forces, such as Van der Waals interactions, ionic interaction, hydrogen bonding, or hydrophobic interaction.

The polymer chains are typically hydrophilic or contain hydrophilic polymer blocks. "Gel-forming polymers" is used to describe any biocompatible polymer, including homopolymers, copolymers, and combinations thereof, capable of forming a physical hydrogel in an aqueous medium when present at or above the critical gel concentration (CGC).

The "critical gel concentration", or "CGC", as used herein, refers to the minimum concentration of gel-forming polymer needed for gel formation, e.g. at which a solution-to-gel (sol-gel) transition occurs. The critical gel concentration can be dependent on a number of factors, including the specific polymer composition, molecular weight, temperature, and/or the presence of other polymers or excipients.

The term "thermosensitive gel-forming polymer" refers to a gel-forming polymer that exhibits one or more property changes with a change in the temperature. For example, some thermosensitive gel-forming polymers are water soluble below a certain temperature but become water insoluble as temperature is increased. The term "lower critical solution temperature (LCST)" refers to a temperature, below which a gel-forming polymer and solvent are completely miscible and form a single phase. For example, "the LCST of a polymer solution" means that the polymer is uniformly dispersed in a solution at that temperature (i.e., LCST) or lower, but aggregates and forms a second phase when the solution temperature is increased beyond the LCST.

"Hydrophilic," as used herein, refers to molecules which have a greater affinity for, and thus solubility in, water as compared to organic solvents. The hydrophilicity of a compound can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the water than in the organic solvent, then the compound is considered hydrophilic.

"Hydrophobic," as used herein, refers to molecules which have a greater affinity for, and thus solubility in, organic solvents as compared to water. The hydrophobicity of a compound can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the organic solvent than in the water, then the compound is considered hydrophobic.

As used herein, the term "treating" includes inhibiting, alleviating, preventing or eliminating one or more symptoms or side effects associated with the disease, condition, or disorder being treated.

The term "reduce", "inhibit", "alleviate" or "decrease" are used relative to a control. One of skill in the art would readily identify the appropriate control to use for each experiment. For example a decreased response in a subject or cell treated with a compound is compared to a response in subject or cell that is not treated with the compound.

As used herein the term "effective amount" or "therapeutically effective amount" means a dosage sufficient to treat, inhibit, or alleviate one or more symptoms of a disease state being treated or to otherwise provide a desired pharmacologic and/or physiologic effect. The precise dosage will vary according to a variety of factors such as subject-dependent variables (e.g., age, immune system health, etc.), the disease or disorder, and the treatment being administered. The effect of the effective amount can be relative to a control. Such controls are known in the art and discussed herein, and can be, for example the condition of the subject prior to or in the absence of administration of the drug, or drug combination, or in the case of drug combinations, the effect of the combination can be compared to the effect of administration of only one of the drugs.

"Excipient" is used herein to include any other compound that can be contained in or on the microparticle that is not a therapeutically or biologically active compound. As such, an excipient should be pharmaceutically or biologically acceptable or relevant, for example, an excipient should generally be non-toxic to the subject. "Excipient" includes a single such compound and is also intended to include a plurality of compounds.

The term "osmolarity", as generally used herein, refers to the total number of dissolved components per liter. Osmolarity is similar to molarity but includes the total number of moles of dissolved species in solution. An osmolarity of 1 Osm/L means there is 1 mole of dissolved components per L of solution. Some solutes, such as ionic solutes that dissociate in solution, will contribute more than 1 mole of dissolved components per mole of solute in the solution. For example, NaCl dissociates into $Na^+$ and $Cl^-$ in solution and thus provides 2 moles of dissolved components per 1 mole of dissolved NaCl in solution. Physiological osmolarity is typically in the range of about 280 to about 310 mOsm/L.

The term "tonicity", as generally used herein, refers to the osmotic pressure gradient resulting from the separation of two solutions by a semi-permeable membrane. In particular, tonicity is used to describe the osmotic pressure created across a cell membrane when a cell is exposed to an external solution. Solutes that can cross the cellular membrane do not contribute to the final osmotic pressure gradient. Only those dissolved species that do not cross the cell membrane will contribute to osmotic pressure differences and thus tonicity. The term "hypertonic", as generally used herein, refers to a solution with a higher concentration of solutes than is present on the inside of the cell. When a cell is immersed into a hypertonic solution, the tendency is for water to flow out of the cell in order to balance the concentration of the solutes. The term "hypotonic", as generally used herein, refers to a solution with a lower concentration of solutes than is present on the inside of the cell. When a cell is immersed into a hypotonic solution, water flows into the cell in order to balance the concentration of the solutes. The term "isotonic", as generally used herein, refers to a solution wherein the osmotic pressure gradient across the cell membrane is essentially balanced. An isotonic formulation is one which has essentially the same osmotic pressure as human blood. Isotonic formulations will generally have an osmotic pressure from about 250 to 350 mOsm.

II. Hypotonic Gel-Forming Compositions

Hypotonic formulations of hydrogel forming polymers, preferably poloxamers, have been developed for enhanced delivery through mucus of therapeutic, diagnostic, prophylactic or other agents, to epithelial tissues, especially those having a mucosal coating. The polymers are administered at a concentration at or higher than their normal critical gelling concentration (CGC). A Poloxamer gel administered into the vagina or colorectum at its CGC will form a "plug" of gel in the lumen. In contrast, fluid from a hypotonically-administered Poloxamer solution below the CGC will be absorbed by the epithelial surface, drawing the Poloxamer into the mucus gel and up against the epithelium, thereby enhancing and facilitating delivery of agents to the epithelial cells. As the Poloxamer is concentrated, it mixes with mucus. The endogenous mucin glycopolymers affect the gelling properties of the hypotonic gelling agents, including the concentration of gelling agent needed to gel and the pore structure of the resulting gel/mucin mixture. After vaginal and colorectal application, the hypotonic gelling vehicles coat the epithelium, including the folds. The examples demonstrate longer vaginal retention of a model drug administered in a hypotonic gelling agent compared to a bolus of gel formed in the middle of the vaginal lumen, as would be the case for a gelling agent administered at the CGC.

The gel-forming compositions contain one or more gel-forming polymers in a hypotonic carrier, optionally containing one or more additional excipients and/or one or more therapeutic, prophylactic, or diagnostic agents.

A. HydroGel-Forming Polymers

The hypotonic gel-forming compositions contain one or more gel-forming polymers. Gel-forming polymers are utilized at a concentration below the normal critical gel concentration (CGC) of the polymer, e.g. the concentration at which the polymer solution would gel in a test tube when warmed to 37° C.

Thermosensitive (aka thermoresponsive) hydrogels are solutions that undergo sol-gel transitions when 1) at or above the critical gelling concentration (CGC) AND 2) at or above the critical gelling temperature. Thermosensitive gelling agents (at or above their CGC) used for biomedical applications are liquid at room temperature, but form a gel at body temperature. The increase in temperature induces a rearrangement and alignment of the polymer chains, leading to gelation into a 3-dimensional structure. This phenomenon is generally governed by the ratio of hydrophilic to hydrophobic moieties on the polymer chain. A common characteristic is the presence of a hydrophobic methyl, ethyl, or propyl group. Any thermosensitive polymer that fits these criteria can be administered hypotonically below the CGC to mucosal epithelial and form a uniform gel coating in vivo. Examples of thermosensitive gel formers that can be used include polyoxyethylene-polyoxypropylene-polyoxyethylene triblock copolymers such as, but not limited to, those designated by the CTFA names Poloxamer 407 (CAS 9003-11-6, molecular weight 9,840-14,600 g/mol; available from BASF as LUTROL® F127) and Poloxamer 188 (CAS 9003-11-6, molecular weight 7680-9510 g/mol; available from BASF as LUTROL® F68); Tetronics tetra-functional block copolymers based on ethylene oxide and propylene oxide available from BASF as Tetronic®; poly(N,N-diethylacrylamide); poly(N,N-dimethylacrylamide); poly(N-vinylcaprolactam); poly(N-alkylacrylamide); poly(N-vinylalkylamide); poly(N-isopropyl acrylamide); polyethylene oxide methacrylate polymers; poly(lactic-co-glycolic acid) (PLGA)-polyethylene glycol triblock copolymers (PLGA-PEG-PLGA and PEG-PLGA-PEG); polycaprolactone (PCL)-polyethylene glycol triblock copolymers (PCL-PEG-PCL and PEG-PCL-PEG); chitosan; and combinations thereof.

The hydrogels can be formed from individual gel formers or as a combination of gel formers. For example, a poloxamer and another gel former (e.g., a tetronic polymer) may be used in combination to attain the desired characteristics. In addition, various forms of the same gel former (e.g., Poloxamer 188 and Poloxamer 407) can be combined to attain the desired characteristics.

The polymer is provided in a concentration less than the concentration that forms a gel in a test tube when heated to 37° C. The concentration must be sufficiently high, but below the CGC, for the epithelium to absorb enough fluid for the CGC to be reached in vivo, so gelation can occur on the mucosal epithelial surface. The range of time that it takes for gelation to occur depends on the mucosal surface (the capacity and rate of water absorption), the tonicity of the solution administered (more hypotonic solutions will drive more rapid fluid absorption), and the concentration of polymer administered (if the polymer concentration is too low, not enough fluid absorption will occur to concentrate the polymer to its CGC). However, gelation generally occurs within 1 h in the vagina and colorectum.

As shown in the examples, 18% F127 gel mixed with purified pig gastric mucins (1%) or human cervicovaginal mucus (1:1 ratio) does not trap virus-sized (~100 nm) nanoparticles (polyethylene glycol coated polystyrene nanoparticles, PSPEG) as effectively as 18% F127 gel alone. In contrast, 24% F98 gel more effectively trapped PSPEG particles when mixed with mucins or human cervicovaginal mucus. However, in vivo viral trapping with hypotonic gelling agents was more effective at trapping viruses, including human immunodeficiency virus (HIV, ~120 nm) and herpes simplex virus (HSV, ~180 nm). Administration of 18% F98, having a CGC of 24%, results in effective trapping of subsequently administered HIV in the vagina. Similarly, 10% and 15% F127, having a CGC of 18%, were also effective in decreasing the MSD of HIV, indicating trapping. Additionally, both 15% F127 and 18% F98 reduced the diffusion of subsequently administered HSV in mouse vaginal mucus. The distribution of the individual virus MSD at a time scale of 1 s illustrated that the trapping (shift to the left) of the viruses was more uniform in the gel formed by the hypotonic 18% F98 vehicle compared to 15% F127. In additional tests of viral trapping by hypotonic gelling agents in the colorectum, it was found that 12% F98 (CGC 24%) did not effectively trap PSPEG nanoparticles administered 30 mins after the gelling vehicle, though 18% F98 was effective at trapping PSPEG nanoparticles in the mouse colorectum. Importantly, these examples illustrate differences in the gels that form when the hypotonic gelling agents are administered to different mucosal surfaces, and in this case, mix with vaginal mucus compared to colorectal mucus prior to gelling.

B. Hypotonic Carriers

The gel-forming compositions include a hypotonic carrier. The hypotonic carrier will typically be a biocompatible carrier that preferably causes little to no signs of irritation when administered to human subjects. The carrier can be naturally occurring or non-naturally occurring including both synthetic and semi-synthetic carriers. Preferred carriers are sodium-based. Other solutions, including sugar-based (e.g. glucose, mannitol) solutions and various buffers (phosphate-buffers, tris-buffers, HEPES), may also be used.

When hypotonic solutions are applied to an epithelial surface, a fluid shift occurs and water is moved into the epithelial tissue. This can cause swelling of the epithelial cells. In some cases, when the osmotic pressure difference is too large, the epithelial cells may burst causing tissue irritation or disruption of the epithelial membrane.

Hypotonic solution refers to a solution that contains less solute compared to the cytoplasm of the cell. Examples of hypotonic solutions include, but are not limited to, Tris [hydroxylmethyl]-aminomethane hydrochloride (Tris-HCl, 10-100 mM, pH. 6-8), (4-(2-hydroxyethyl)-1-piperazineethanesulfonic acid (HEPES, 10-100 mM, pH 6-8) and dilute solutions of PBS, such as a solution containing 0.2 grams KCl, 0.2 grams $KH_2PO_4$, 8 grams NaCl, and 2.16 grams $Na_2HPO_4*7H_2O$ in 1000 ml $H_2O$.

Hypotonic carriers concentrate the gel-forming polymer at an epithelial surface, resulting in uniform gel formation on the surface. The hypotonic carrier usually contains water as the major component. The hypotonic carrier can be water, although mixtures of water and a water-miscible organic solvent can also be used. Suitable water-miscible organic solvents include alcohols, such as ethanol, isopropanol; ketones, such as acetone; ethers, such as dioxane and the like; and esters such as ethyl acetate.

The hypotonic carrier can be distilled water containing one or more osmolarity modifying excipients. Sodium chloride is the excipient that is most frequently used to adjust osmolarity if a solution is hypotonic. Other excipients used to adjust hypotonic solutions include glucose, mannitol, glycerol, propylene glycol and sodium sulphate. Osmolarity modifying excipients can include pharmaceutically acceptable salts such as sodium chloride, sodium sulfate, or potassium chloride. Other excipients used to adjust tonicity can include glucose, mannitol, glycerol, or propylene glycol.

The hypotonic carrier can have any osmolarity less than the effective isotonic point (the concentration at which fluid is neither absorbed nor secreted by the epithelium) at that mucosal surface. The isotonic point varies for different mucosal surfaces and different buffers, depending on active ion transport at that epithelial surface; e.g. we have found that isotonic point in the vagina for sodium-based solutions to be about 300 mOsm/L, but in the colorectum, it is about 450 mOsm/L. In some embodiments the solution has a tonicity from 50 mOsm/L to 280 mOsm/L, from 100 mOsm/L to 280 mOsm/L, from 150 mOsm/L to 250 mOsm/L, from 200 mOsm/L to 250 mOsm/L, from 220 mOsm/L to 250 mOsm/L, from 220 mOsm/L to 260 mOsm/L, from 220 mOsm/L to 270 mOsm/L, or from 220 mOsm/L to 280 mOsm/L.

The hypotonic carrier can include one or more pharmaceutically acceptable acids, one or more pharmaceutically acceptable bases, or salts thereof. Pharmaceutically acceptable acids include hydrobromic, hydrochloric, and sulphuric acids, and organic acids, such as methanesulphonic acids, tartaric acids, and malcic acids. Pharmaceutically acceptable bases include alkali metal (e.g. sodium or potassium) and alkali earth metal (e.g. calcium or magnesium) hydroxides and organic bases such as pharmaceutically acceptable amines. The hypotonic carrier can include pharmaceutically acceptable buffers such as citrate buffers or phosphate buffers.

C. Additional Agents

The hypotonic gel-forming compositions can contain one or more agents to be delivered or incorporated into the hydrogel barrier including therapeutic agents, prophylactic agents, diagnostic agents, and/or nutraceuticals. "Bioactive agent" and "active agent" are used interchangeably include without limitation physiologically or pharmacologically active substances that act locally or systemically in the body. A biologically active agent is a substance used for the treatment (e.g., therapeutic agent), prevention (e.g., prophylactic agent), diagnosis (e.g., diagnostic agent), cure or mitigation of disease or illness, a substance which affects the structure or function of the body, or pro-drugs, which become biologically active or more active after they have been placed in a predetermined physiological environment. Examples can include, but are not limited to, small-molecule drugs, peptides, proteins, antibodies, sugars, polysaccharides, nucleotides, oligonucleotides, aptamers, siRNA, nucleic acids, and combinations thereof. The agents can be a small molecule (e.g., molecular weight less than 2000, 1500, 1000, 750, or 500 atomic mass units (amu)) or a biomolecule, such as peptides, proteins, nucleic acids, polysaccharides, lipids, glycoproteins, lipoproteins, or combinations thereof. The agents can include one or more of those described in *Martindale: The Complete Drug Reference*, $37^{th}$ Ed. (Pharmaceutical Press, London, 2011).

The hypotonic gel-forming formulations can contain a therapeutically effective amount of a therapeutic agent to treat, inhibit, or alleviate one or more symptoms of a disease state being treated. The hypotonic gel-forming compositions can contain an effective amount of a prophylactic agent to prevent one or more symptoms of a disease or disorder.

Exemplary classes of agents include, but are not limited to, synthetic and natural proteins (including enzymes, peptide-hormones, receptors, growth factors, antibodies, signaling molecules), and synthetic and natural nucleic acids (including RNA, DNA, anti-sense RNA, triplex DNA, inhibitory RNA (RNAi), and oligonucleotides), and biologically active portions thereof.

Agents may be anti-infective (antibiotics, antivirals, antifungals), anti-inflammatory, for birth control, for treatment of metabolic disorders, for treatment of heartburn or ulcers, for treatment of cardiovascular disorders such as hypertension and atherosclerosis, neuroactive agents, and chemotherapeutics.

Examples of useful proteins include hormones such as insulin and growth hormones including somatomedins. Examples of useful drugs include neurotransmitters such as L-DOPA, antihypertensives or saluretics such as Metolazone from Searle Pharmaceuticals, carbonic anhydrase inhibitors such as Acetazolamide from Lederle Pharmaceuticals, insulin like drugs such as glyburide, a blood glucose lowering drug of the sulfonylurea class, synthetic hormones such as Android F from Brown Pharmaceuticals and Testred® (methyltestosterone) from ICN Pharmaceuticals. Representative anti-proliferative (anti-cancer or endometriosis) agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), and combinations thereof. Other suitable anti-cancer agents include angiogenesis inhibitors including antibodies to vascular endothelial growth factor (VEGF) such as bevacizumab (AVASTIN®), other anti-VEGF compounds; thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

For imaging, radioactive materials such as Technetium99 ($^{99m}$Tc) or magnetic materials such as labelled-$Fe_2O_3$ could be used. Examples of other materials include gases or gas emitting compounds, which are radioopaque.

III. Methods and Preparations of Hypotonic Gel-Forming Compositions

The formulations can be prepared as liquids for administration. Typically these will be prepared as single or multiple dosage units in an appropriate applicator. Powder units may be dual chambered, one containing solvent, with or without excipients to adjust tonicity, and the other containing the hydrogel forming material, typically also including the one or more agents to be administered. Multiple dosage units will typically include a barrel loaded with powder, and a plunger having dosage increments thereon. These will typically be sterilized and packaged in sealed, sterile packaging for storage and distribution.

Dosage unit administrators may be designed to fit the anatomic location to which drug is to be delivered, such as intrarectally, intravaginally, intranasally, or intrabuccally.

IV. Methods of Administering Hypotonic Gel-Forming Compositions

The hypotonic gel-forming compositions can, in principal, be applied to any water-absorbent surface. In one embodiment, the formulations are applied as a liquid to a mucosal coating on an epithelial surface of a subject in need of a therapeutic, prophylactic, diagnostic, or nutritional effect. The gel-forming composition can be applied in any number of ways known to the skilled artisan as long as the hypotonic solution, or reagents forming the hypotonic solution, contacts the surface. By applying the gel-forming compositions as a hypotonic formulation, water is absorbed into the epithelial tissue. Water absorption provides for concentration of the gel-forming polymer at the surface, resulting in uniform gel formation at the surface. In another embodiment, the gel is applied as it solidifies or in a partially solid form, thereby acting as a barrier, reservoir or depo, or combination thereof. Agents or excipients in the gel-forming composition can become entrapped in the gel and can be released at or into the surface.

The hypotonic gel-forming compositions can be applied to any epithelial surface. Applying the gel-forming composition as a hypotonic solution results in water absorption by the epithelial cells and gel formation at the epithelial surface. The epithelial surface can include oral surfaces, pharyngeal surfaces, esophageal surfaces, pulmonary surfaces, ocular surfaces, aural surfaces, nasal surfaces, buccal surfaces, lingual surfaces, vaginal surfaces, cervical surfaces, genitourinary surfaces, alimentary surfaces, anorectal surfaces, and/or skin surfaces. Preferred routes of administration include rectal and vaginal, or other mucosal coated surfaces.

The present invention will be further understood by reference to the following non-limiting examples.

EXAMPLES

Example 1. Non-Adhesive Nanoparticle Transport is Enhanced in Various Thermosensitive Gel Formulations Materials and Methods Non-adhesive nanoparticles (PSPEG) were used to assess the pore structure of multiple thermosensitive PLURONIC® gels at their CGC. The thermosensitive PLURONIC® gels tested included 15% F68, 24% P104, 18% F68/15% F127, 24% F98, and 18% F127. Multiple particle tracking (MPT) was used to observe the motions of PSPEG in the gels, incubated in a temperature-controlled chamber set to 37° C. The data was reported as ensemble averaged mean-squared displacement (<MSD>, $\mu m^2$) as a function of time scale in seconds (s).

Fluorescent, carboxylate-modified polystyrene nanoparticles (PS—COOH) 100 nm in size were densely coated with poly(ethylene glycol) (PEG) to produce non-adhesive PEG-coated PS nanoparticles (PSPEG). Briefly, 5 kDa methoxy-PEG-amine, N-Hydroxysulfosuccinimide, and 1-Ethyl-3-(3-dimethylaminopropyl) carbodiimide were dissolved in 200 mM borate buffer and added to PS—COOH to facilitate coupling of carboxylic acid and amine groups. Nanoparticle size was characterized using dynamic light scattering (90° scattering angle), and ζ-potential was determined via laser Doppler anemometry with a Zetasizer Nano ZS90.

Results

As shown in FIG. 1, the MSD of 100 nm PSPEG varied significantly for the different gels tested, with particles diffusing the fastest in 15% F68 gel and the slowest in 18% F127 gel. FIGS. 2A-2E display typical trajectories for a 100 nm PSPEG in the various gels, supporting the ranges of average MSD values calculated for nanoparticles in each gel. PSPEG could diffuse relatively rapidly in 15% F68 gel, whereas the nanoparticles were completely immobilized in 18% F127 gel (Table 1). Gels that immobilize particles this size may have steric barrier properties to nano-sized objects (including viruses), whereas gels that are permissive to nanoparticle diffusion may be suitable for administering nanoparticles that must be delivered to the epithelium and taken up by cells.

TABLE 1

Transport of 100 nm (hydrodynamic radius 120 nm) PSPEG in various thermogelling vehicles at 37° C. Larger numbers indicate slowing of the nanoparticles. Values are representative of n ≥ 3 samples.

| Gel Type | $MSD_w/MSD_g$ |
|---|---|
| 15% F68 | 6 |
| 24% P104 | 15 |
| 18% F68/15% F127 | 48 |
| 24% F98 | 280 |
| 18% F127 | 1800 |

$MSD_w$—theoretical MSD of nanoparticles in water
$MSD_g$—average MSD of the nanoparticles in the gel sample.

Example 2. Changes in Gel Pore Size in the Presence of Mucin Glycopolymers

The difference between the Poloxamer gels at their critical gelling concentration (CGC), as they are normally administered, and the Poloxamer gels in a hypotonic solution below their CGC was investigated. A Poloxamer gel administered into the vagina or colorectum at its CGC will form a "plug" of gel in the lumen. In contrast, fluid from a hypotonically-administered Poloxamer solution below the CGC will be absorbed by the epithelial surface, drawing the Poloxamer into the mucus gel and up against the epithelium. As the Poloxamer is concentrated, it mixes with mucus. It was hypothesized that mixing with the endogenous mucin glycopolymers would affect the gelling properties of the hypotonic gelling agents, including the concentration of gelling agent needed to gel and the pore structure of the resulting gel/mucin mixture.

The pore structure of the gels may be altered by mixing with mucin glycopolymers, such as those found in the mucus layers on epithelial cells, particularly when the gelling vehicle is administered hypotonically below the CGC. To test for the changes in pore structure of the gels following application of the gels to different concentrations of mucins, the following study was performed.

Materials and Methods

Non-adhesive nanoparticles (PSPEG) were used to assess the pore structure of multiple thermosensitive Poloxamer gels at their CGC, including 15% F68, 24% P104, 18% F68/15% F127, 24% F98, and 18% F127. Multiple particle tracking (MPT) was used to observe the motions of PSPEG in the gels, incubated in a temperature-controlled chamber set to 37° C.

Similar MPT experiments as those in Example 1 were performed at 37° C. with 100 nm PSPEG particles and gels mixed with 1% porcine gastric mucin (commercially available) or mixed 1:1 with human cervicovaginal mucus (CVM) (50% mucus).

Results

Figure 3:
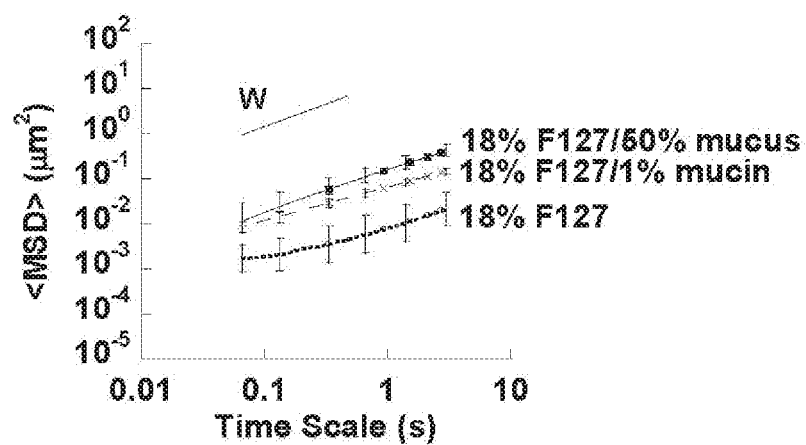
FIG. 3 is a line graph showing transport properties of 100 nm PSPEG nanoparticles in thermogelling vehicles mixed with 1% purified pig gastric mucin or at a 1:1 ratio with human CVM at 37° C. Ensemble mean-squared displacement (<MSD>, $\mu m^2$) as a function of time scale (s) for 100 nm PSPEG in 18% F127 containing 1% mucin or 50% CVM (50% mucus) is presented. Data is representative of n≥3 samples. W represents the theoretical diffusion of the PSPEG nanoparticles in water.
Figure 4:
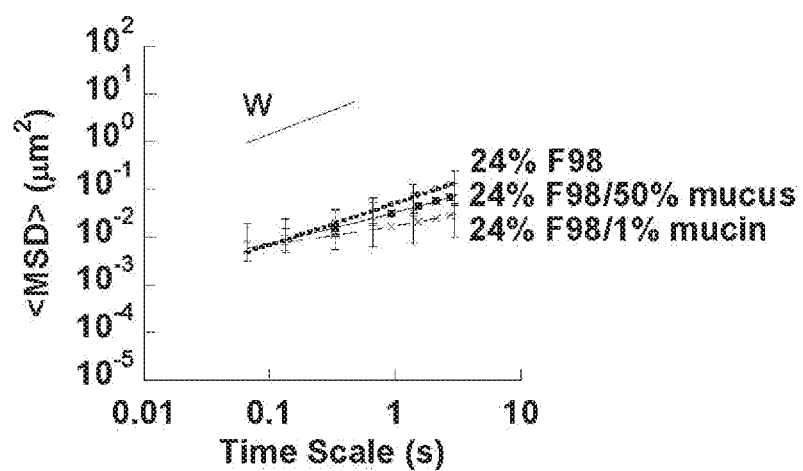
FIG. 4 is a line graph showing transport properties of 100 nm PSPEG nanoparticles in thermogelling vehicles mixed with 1% purified pig gastric mucin or at a 1:1 ratio with human CVM at 37° C. Ensemble mean-squared displacement (<MSD>, $\mu m^2$) as a function of time scale (s) for 100 nm PSPEG in 24% F98 containing 1% mucin or 50% CVM (50% mucus) is presented. Data is representative of n≥3 samples. W represents the theoretical diffusion of the PSPEG nanoparticles in water.

As shown in FIG. 3, the structure of 18% F127 gel was significantly affected by mixing the polymer with mucin or mucus. The 100 nm PSPEG became more mobile in the presence of mucin/mucus, indicating an increase in pore size of the gel. In contrast, 24% F98 gel pore structure was not significantly affected by mucin or mucus (FIG. 4), as the mobility of the particles was not changed in the presence of mucin/mucus. The trajectories of 100 nm PSPEG became more diffusive when 18% F127 was mixed with mucin/mucus, whereas 100 nm PSPEG were similarly immobilized in 24% F98 with mucin/mucus.

Example 3. Entrapment of Viruses by the Hypotonic PLURONIC® Gelling Agents Gelled Against the Epithelium The ability of hypotonic PLURONIC® gelling agents to gel against the epithelium and trap viruses after administration to the mouse vagina were investigated. Trapping would only occur if the fluid absorption by the epithelium was significant enough to concentrate the PLURONIC® solutions to their CGC and induce gelling, and mixing with the mucus present in the colorectum did not increase the pores in the gel to a diameter larger than the viruses.

Materials and Methods

The trapping of both fluorescently labeled human immunodeficiency virus (HIV, ~120 nm) and herpes simplex virus type 1 (HSV, ~180 nm) were tested.

HSV-1 virus was produced by Prashant Desai (Johns Hopkins University). The recombinant virus expresses red fluorescent protein (RFP) internally (Desai, P.; Sexton, G. L.; Huang, E.; Person, S., Localization of herpes simplex virus type 1 UL37 in the Golgi complex requires UL36 but not capsid structures. *J Virol* 2008, 82, 11354-6), so the fluorescent label should not affect interactions between the viral surface and gel/mucus.

HIV virus was produced by Samuel Lai (University of North Carolina). The recombinant virus internally expresses mCherry fluorophore fused to Gag structural protein or Vpr accessory protein pseudotyped with YU2 Env. Similarly, the fluorescent label should not affect interactions between the viral surface and gel/mucus.

Results

Figure 5:
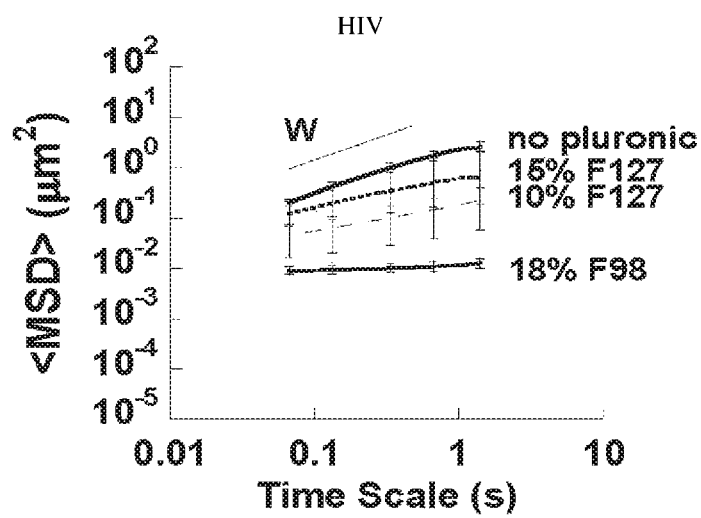
FIG. 5 is a line graph showing transport properties of fluorescently labeled HIV virions introduced after administration of 15% and 10% F127 and 18% F98 to the vagina (all below CGC), compared to virus diffusion without gelling agents (no pluronic). Ensemble averaged mean-squared displacement (<MSD>, $\mu m^2$) as a function of time scale (s) for HIV administered <5 min after hypotonic gelling agents. W represents the theoretical diffusion of HIV in water.
Figure 6:
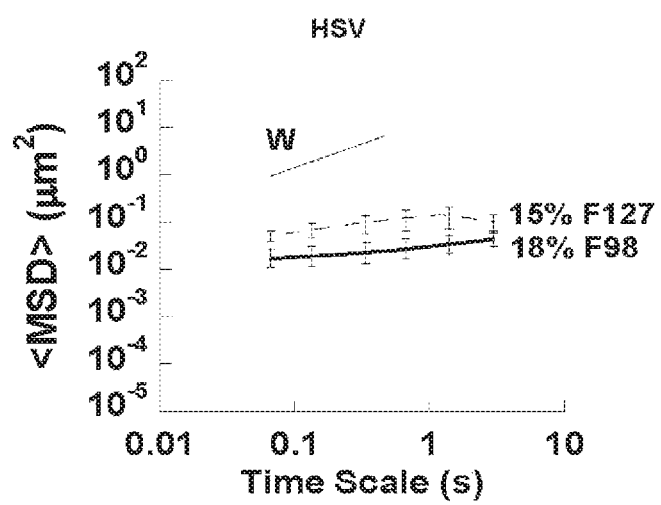
FIG. 6 is a line graph showing transport properties of fluorescently labeled HSV virions introduced after administration of 15% F127 and 18% F98 (all below CGC) to the vagina. Ensemble averaged mean-squared displacement (<MSD>, $\mu m^2$) as a function of time scale (s) for HSV administered <5 min after hypotonic gelling agents. W represents the theoretical diffusion of HSV in water.
Figure 7A:
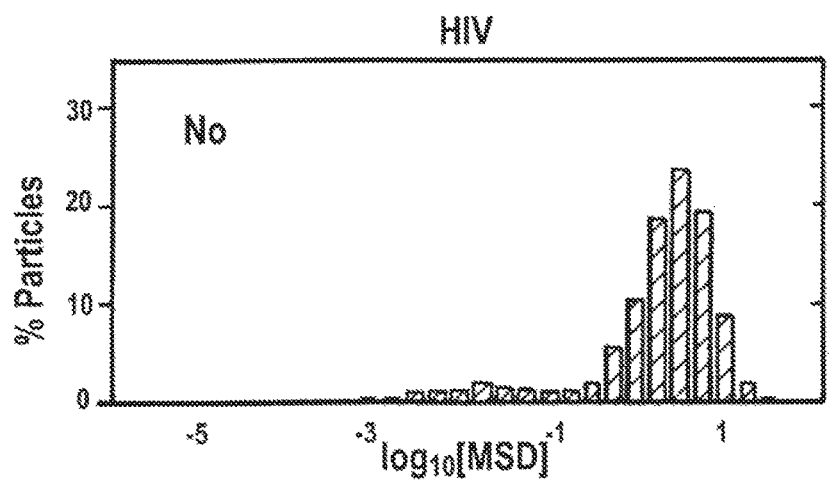
FIGS. 7A-7F are bar graphs of the distribution of the logarithmic MSD of individual HSV and HIV virions at a time scale of 1 s. Virions were administered <5 mins after administration of 18% F98 or 15% F127, compared to administration of viruses without gel (diffusion of the viruses in vaginal mucus alone).
Figure 7B:
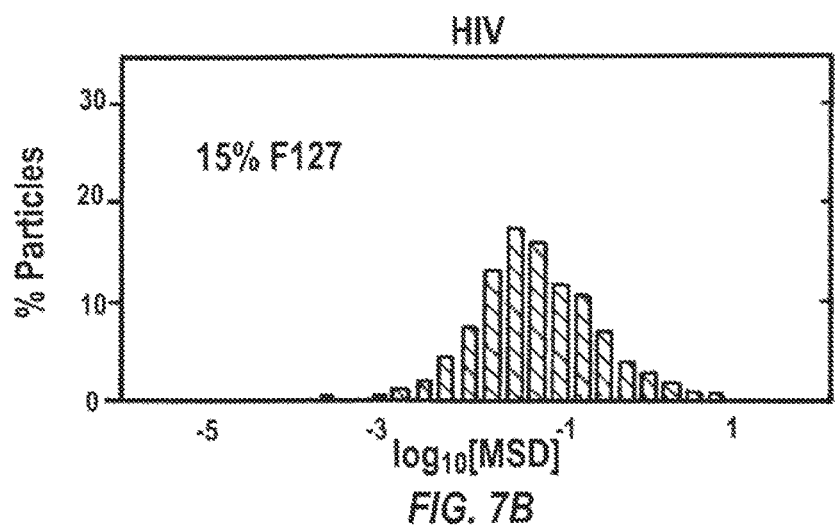
Figure 7C:
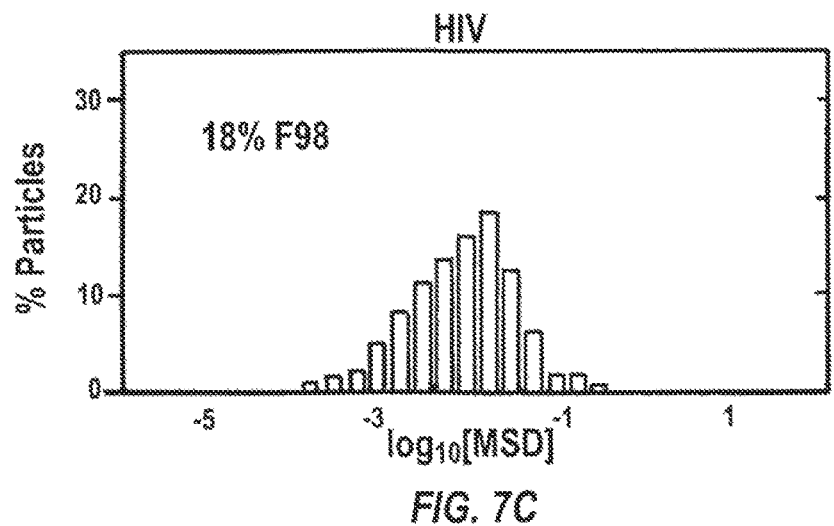
Figure 7D:
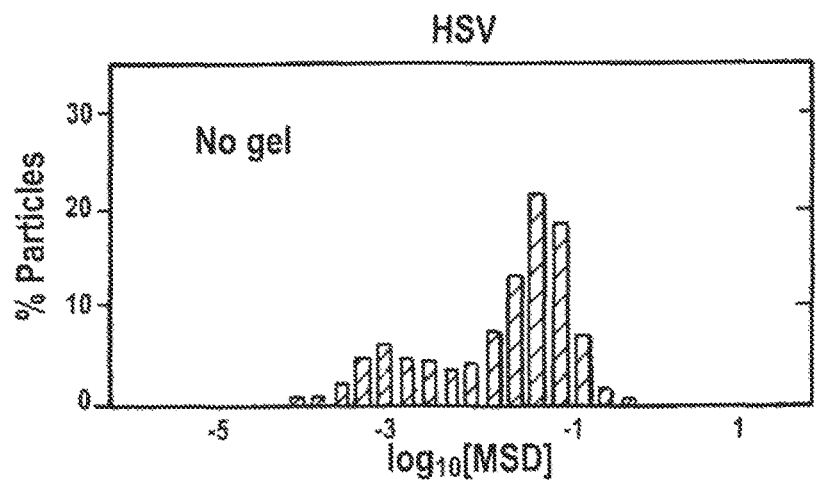
Figure 7E:
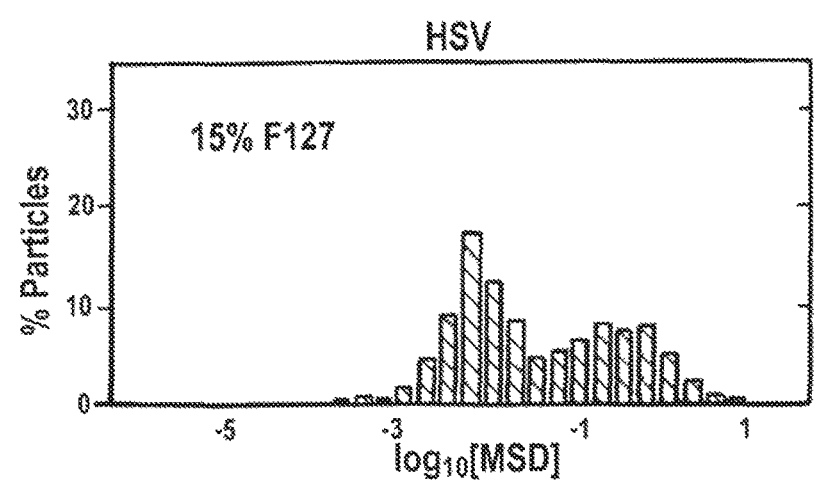
Figure 7F:
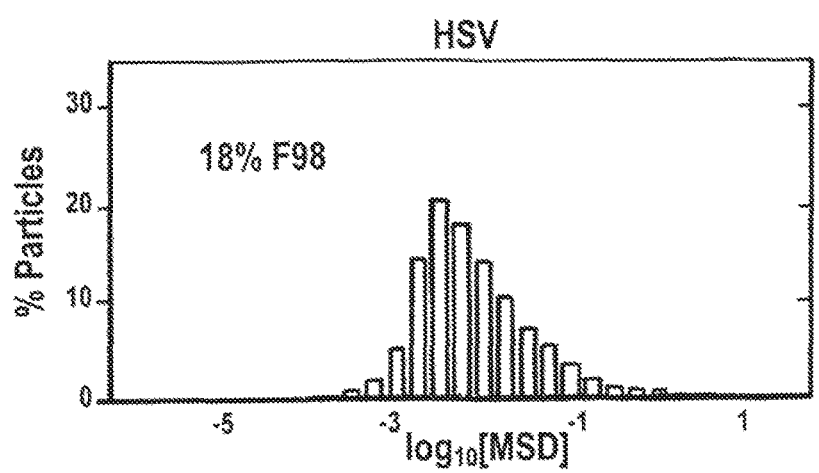

As shown in FIG. 5, HIV diffuses in mouse vaginal mucus without gel. Administration of 10% and 15% F127 (the CGC is 18%) results in a modest decrease in the MSD. As shown in FIG. 3, F127 gel mixed with mucus does not efficiently trap virus-sized particles. In contrast, administration of 18% F98 (the CGC is 24%) results in effective trapping of subsequently administered HIV in the vagina. For HSV, which is larger in size, both 15% F127 and 18% F98 reduce the diffusion of HSV, but 18% F98 was more effective at trapping HSV (FIG. 6).

Example 4. Testing of Transport Properties of Hypotonic Gelling Agents in Colorectum Materials and Methods Additional tests of trapping PSPEG nanoparticles or HIV by the hypotonic gelling agent in the colorectum were performed. PSPEG nanoparticles were prepared as described in Example 1. HIV was prepared as described in Example 3.

Results

Figure 8:
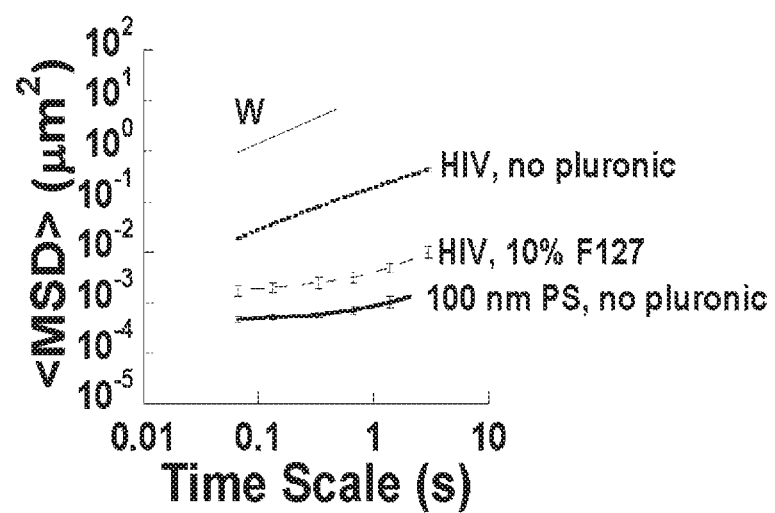
FIG. 8 is a line graph showing the mean squared displacement (<MSD>, $\mu m^2$) as a function of time scale (s) for HIV virions in mouse colorectal mucus (HIV, no pluronic) or in the colorectum after administration of hypotonic gelling agent (HIV, 10% F127). The virus was immobilized in the presence of gel, similar to mucoadhesive polystyrene (PS) nanoparticles that become adhesively trapped in mucus (100 nm PS, no pluronic).

Fluorescently-labeled HIV diffused rapidly through mouse colorectal mucus, but if a hypotonic solution of gelling agent below the CGC (10% F127) was introduced prior to virus, the virus was immobilized (>500 fold slower movement than virus without gel) similarly to nanoparticles that are adhesively trapped in mucus, 100 nm PS nanoparticles (FIG. 8).

Figure 9:
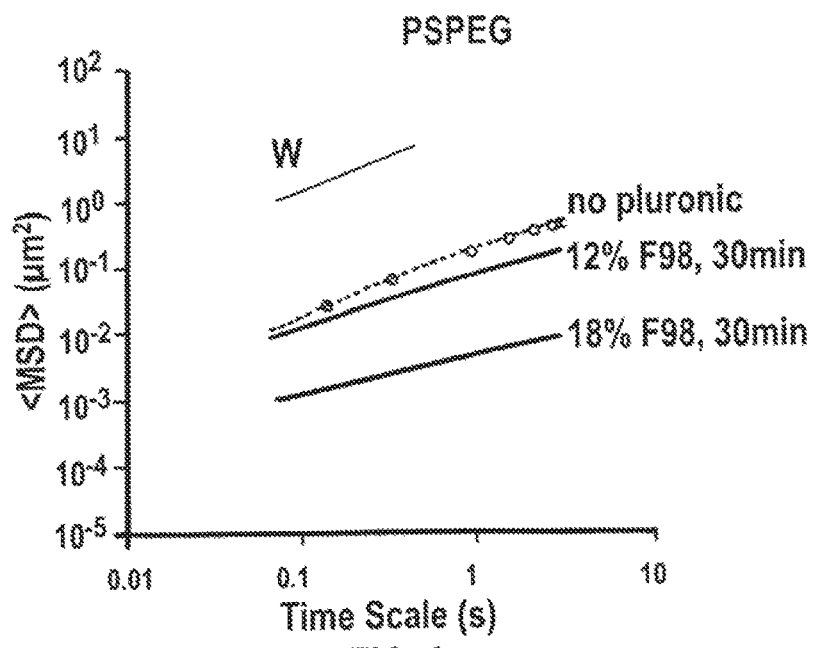
FIG. 9 is a line graph showing transport properties of 100 nm PSPEG administered 30 min after hypotonic gelling vehicles to the colorectum. Ensemble averaged mean-squared displacement (<MSD>, $\mu m^2$) as a function of time scale (s) for 100 nm PSPEG 30 min after rectal administration of 12% or 18% F98, and compared to transport of 100 nm PSPEG in colorectal mucus alone (no pluronic).
Figure 10:
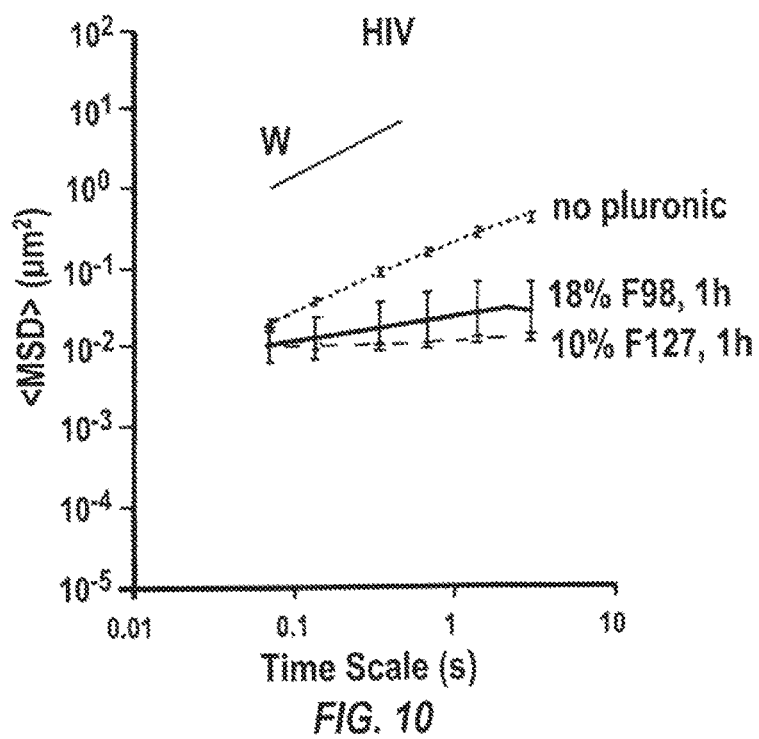
FIG. 10 is a line graph showing transport properties of fluorescently-labeled HIV virions administered 1 h after administration of 18% F98 and 10% F127 to the colorectum. Ensemble averaged mean-squared displacement (<MSD>, μm$^2$) as a function of time scale (s) for HIV, compared to diffusion in mouse colorectal mucus alone (no pluronic).

It was found that 12% F98 was too dilute to effectively reach the CGC for F98 (24%), though 18% F98 was concentrated enough, based on trapping of 100 nm PSPEG (FIG. 9). In addition, both 18% F98 and 10% F127 were effective at trapping HIV administered 1 h after the gelling agent (FIG. 10). This phenomenon highlights specific differences in the gels that form when mixing the hypotonic gelling agents with vaginal mucus compared to colorectal mucus.

Example 5. Increased Retentions of a Model Drug Fluorescein by Hypotonic Gelling Agents after Vaginal Application After vaginal application, the hypotonic gelling vehicles coat the epithelium, including the vaginal folds, and may lead to longer vaginal retention compared to a bolus of gel formed in the middle of the vaginal lumen (as would be the case for a gelling agent administered at the CGC).

Materials and Methods

Fluorescein was administered in either deionized (DI) water, thermogel at the CGC (18% F127), or hypotonic thermogel (10% F127) and retention was assessed at 24 h. Percent fluorescence retained (%) was normalized based on fluorescence immediately after administration. Data were representative of n=3 experiments with n≥3 mice each.

Results

Figure 11:
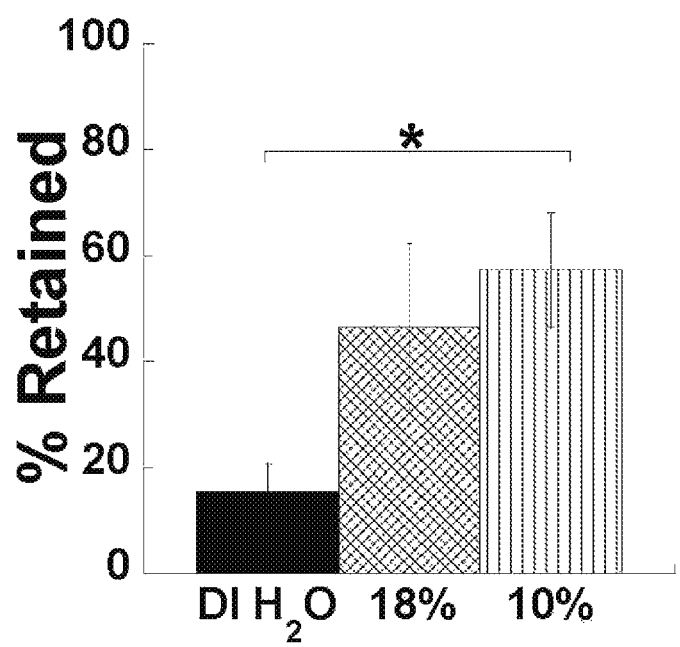
FIG. 11 is a graph of percent retention of a model fluorescent drug in the mouse vagina. Fluorescein was administered in either DI water, thermogel at the CGC (18% F127), or hypotonic thermogel (10% F127) and retention was assessed 24 h later. The percent fluorescence retained (%) was normalized based on fluorescence immediately after administration. Data are representative of n=3 experiments with n≥3 mice each. *P<0.05 compared to deionized water control.

As shown in FIG. 11, hypotonic gelling agent F127 at 10% provided increased vaginal retention of a model drug, fluorescein, after 24 h compared to fluorescein in F127 administered at its CGC (18%). Both gels retained fluorescein longer in the vagina than administration in water.

Example 6. Cytokine Release after Daily Vaginal Application of Hypotonic Gelling Agents Toxicity is a significant concern when designing products for application to mucosal surfaces. Vaginal toxicity and irritation from certain microbicide products actually increases susceptibility to sexually transmitted infections rather than providing protection (Segarra et al., *PLoS One*, 6(11), e27675, 2011). Nonoxynol-9 (N9), a product known to increase susceptibility to vaginal HIV infection, causes release of the cytokine IL-1β (released in response to epithelial injury) after daily vaginal administration for 7 days in mice (Ensign et al., *Sci Transl Med*, 4(138):138ra79, 2012).

Therefore, IL-1β cytokine release following daily vaginal administration of hydroxyethylcellulose placebo gel, 1% F127, 18% F127, and 5% N9 was evaluated after 7-day application.

Materials and Methods

Twenty μL of each test agent was administered intravaginally to progestin-induced diestrus phase (DP) mouse model once a day for seven days (L. M. Ensign, B. C. Tang, Y. Y. Wang, T. A. Tse, T. Hoen, R. Cone, J. Hanes, Mucus-penetrating nanoparticles for vaginal drug delivery protect against herpes simplex virus, Science Translational Medicine, 4 (2012) 138ra179). On the eighth day, each mouse was lavaged twice with 50 μL of PBS. Each lavage sample was diluted with an additional 200 μL of PBS and centrifuged to remove the mucus plug. Supernatant (50 μL) was used to measure the concentration of IL-1β using Quantikine ELISA kits (R&D Systems). ELISAs were conducted as per manufacturer's instructions.

Results

Figure 12:
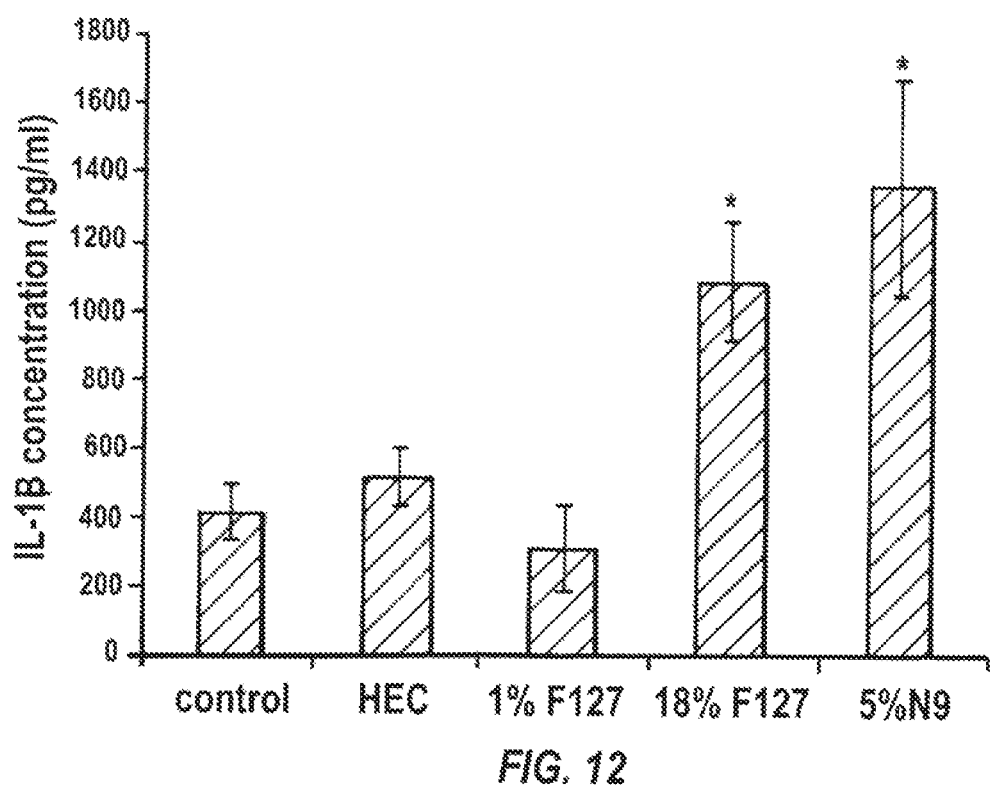
FIG. 12 is a bar graph showing the concentration of cytokine IL-1β in mouse cervicovaginal lavage fluid after daily vaginal administration of hydroxyethylcellulose universal placebo gel (HEC), 1% F127, 18% F127, and 5% nonoxynol-9 (N9) for 7 days. *P<0.05 compared to no treatment control, Student's t-test.

It was found that daily application for 7 days of 18% F127 caused IL-1β release similar to 5% N9, likely indicating that there was epithelial irritation that could lead to an increase in susceptibility to infection. In contrast, products like the hydroxyethylcellulose placebo gel often used as the placebo in HIV clinical trials and 1% F127 solution had cytokine release indistinguishable from the no treatment control (FIG. 12). This result indicated that a hypotonic 1% F127 solution would be a safer vaginal in situ gelling product than products containing F127 concentrations above the CGC.

Results

As shown in FIG. 12A, the MSD of 100 nm PSPEG varied significantly for the different gels tested, with particles diffusing the fastest in 15% F68 gel and the slowest in 18% F127 gel. FIG. 12B displays a typical trajectory for a 100 nm PSPEG in the various gels, supporting the ranges of average MSD values calculated for nanoparticles in each gel. PSPEG could diffuse relatively rapidly in 15% F68 gel, whereas the nanoparticles were completely immobilized in 18% F127 gel (Table 2). Gels that immobilize particles this size may have steric barrier properties to nano-sized objects (including viruses), whereas gels that are permissive to nanoparticle diffusion may be suitable for administering nanoparticles that must be delivered to the epithelium and taken up by cells.

However, the pore structure of the gels may be altered by mixing with mucin glycopolymers, particularly when the gelling vehicle is administered hypotonically below the CGC, as a delivery vehicle. Thus, similar MPT experiments were performed at 37° C. with 100 nm PSPEG particles and gels mixed with 1% porcine gastric mucin (commercially available) or mixed 1:1 with human cervicovaginal mucus (CVM) (50% mucus). As shown in FIG. 1A, the structure of 18% F127 gel was significantly affected by mixing the polymer with mucin or mucus; the 100 nm PSPEG became more mobile in the presence of mucin/mucus. In contrast, 24% F98 gel pore structure was not significantly affected by mucin or mucus (FIG. 1A). This is further illustrated in FIG. 1B, as the trajectories of 100 nm PSPEG became more diffusive when 18% F127 was mixed with mucin/mucus, whereas 100 nm PSPEG were similarly immobilized in 24% F98 with mucin/mucus. For the use of hypotonic gelling agents as a physical barrier to viruses, the increase in F127 gel pore size upon mixing with mucus would not be ideal. However, this may be advantageous for use as a delivery vehicle for nanoparticles. The gelling vehicles are administered at concentrations below the CGC. The gelling agents concentrate to the CGC as fluid is absorbed, which would occur in contact with the mucus lining the epithelial surfaces of the vagina and colorectum.

Whether the hypotonic Poloxamer gelling agents would be able to gel against the epithelium and trap virus after administration to the mouse vagina was then investigated. Trapping would only occur if the fluid absorption by the epithelium was significant enough to concentrate the Poloxamer solutions to their CGC and induce gelling, and mixing with the mucus present in the colorectum did not increase the pores in the gel to a diameter larger than the viruses. Trapping of both fluorescently labeled human immunodeficiency virus (HIV, ~120 nm) and herpes simplex virus type 1 (HSV, ~180 nm) was tested. As shown in FIG. 3A, HIV diffuses in mouse vaginal mucus without gel, and administration of 10% and 15% F127 (the CGC is 18%) results in a modest decrease in the MSD. As shown in FIG. 2, F127 gel mixed with mucus does of efficiently trap virus-sized particles. In contrast, administration of 18% F98 (the CGC is 24%), results in effect trapping of subsequently administered HIV in the vagina. For HSV, which is larger in size, both 15% F127 and 18% F98 reduce the diffusion of HSV, but 18% F98 was more effective at trapping HSV (FIG. 3B). The distribution of the individual virus MSD at a time scale of 1 s further illustrated the trapping (shift to the left) of the viruses when the hypotonic gelling agents were administered vaginally 1 h prior to viruses.

In additional tests of trapping by the hypotonic gelling agent in the colorectum, it was found that 12% F98 was too dilute to effectively reach the CGC for F98 (24%), though 18% F98 was concentrated enough, based on trapping of 100 nm PSPEG (FIG. 4A). It was then discovered that both 18% F98 and 10% F127 were effective at trapping HIV administered 1 h after the gelling agent (FIG. 4B). This phenomenon highlights specific differences in the gels that form when mixing the hypotonic gelling agents with vaginal mucus compared to colorectal mucus.

Looking at the gelling vehicles from a drug delivery standpoint, it was hypothesized that the hypotonic gelling vehicles would coat the epithelium, including the vaginal folds, which would lead to longer vaginal retention compared to a bolus of gel formed in the middle of the vaginal lumen (as would be the case for a gelling agent administered at the CGC). Indeed, as shown in FIG. 5, we found that 10% F127 provided increased vaginal retention of a model drug, fluorescein, after 24 h compared to fluorescein in F127.

We claim:

1. An aqueous hypotonic polymeric formulation for use as a barrier and/or in the delivery of a therapeutic, prophylactic, diagnostic or nutraceutical agent to a mucosal or epithelial surface comprising:
   a gel-forming polymer that is a block copolymer comprising at least one unit that is polyoxyethylene or polyoxypropylene at a concentration which is less than the critical gel concentration of the polymer at the time of application to the mucosal or epithelial surface, which increases in concentration as water is absorbed from the formulation to or above the critical gel concentration of the polymer and a temperature between room temperature and body temperature, thereby forming a gel on the mucosal or epithelial surface,
   one or more excipients forming a hypotonic formulation of the polymer, and
   a therapeutic, prophylactic, diagnostic or nutraceutical agent.

2. A hypotonic gel on a mucosal or epithelial surface formed by diffusion of water from an aqueous hypotonic polymeric formulation comprising:
   a gel-forming polymer that is a block copolymer comprising at least one unit that is polyoxyethylene or polyoxypropylene at a concentration which is less than the critical gel concentration of the polymer at the time of application to the mucosal or epithelial surface, which increases in concentration as water is absorbed from the formulation to or above the critical gel concentration of the polymer at a temperature between room temperature and body temperature, thereby forming a gel on the mucosal or epithelial surface,
   one or more excipients forming a hypotonic formulation of the polymer, and
   a therapeutic, prophylactic, diagnostic or nutraceutical agent.

3. The formulation of claim 1, wherein the gel-forming polymer is a thermosensitive gel-forming polymer.

4. The formulation of claim 3, wherein the thermosensitive gel-forming polymer has a lower critical solution temperature that is below 30° C.

5. The formulation of claim 1 wherein the polymer is a poloxamer.

6. The formulation of claim 1, wherein the mucosal or epithelial surface is selected from the group consisting of oral, pharyngeal, esophogeal, pulmonary, ocular, aural, nasal, buccal, lingual, vaginal, cervical, genitourinary, alimentary, anorectal, and skin surfaces.

7. The formulation of claim 6, wherein the mucosal or epithelial surface is the vaginal surface and the prophylactic or therapeutic effect is contraception, protection against sexually-transmitted disease, or treatment of abnormal proliferation.

8. The formulation of claim 1, comprising a therapeutic agent.

9. The gel of claim 2, wherein the gel releases the therapeutic, prophylactic, diagnostic or nutraceutical agent at the mucosal or epithelial surface over a period of at least 24 hours.

10. The formulation of claim 1, wherein the gel-forming polymer is between greater than 12 and less than 24% polyoxyethylene-polyoxypropylene-polyoxyethylene triblock polymer with an average molecular weight Mw of 13,000 Da and an average weight percent of polyoxyethylene at 80%.

11. The formulation of claim 1, wherein the gel-forming polymer is between 10 and 18% Poloxamer 407.

12. The formulation of claim 1, wherein the gel forms a uniform layer on the mucosal or epithelial surface.

13. The formulation of claim 1, wherein the gel causes no significant signs of irritation at the mucosal or epithelial surface.

14. A method for making an aqueous hypotonic polymeric formulation of claim 1 comprising: combining water with a dry powder formulation comprising a gel-forming polymer that is a block copolymer comprising at least one unit that is polyoxyethylene or polyoxypropylene, and tonicity modifying excipients.

15. The formulation of claim 1, wherein the formulation is provided in a single or multiple dosage unit.

16. A method for administering an agent to a mucosal or epithelial surface comprising administrating to a site in need thereof the formulation of claim 1.

17. The method of claim 16 wherein the concentration of the polymer in the formulation at the time of administration to the site in need thereof is less than the critical gel concentration of the polymer.

18. The method of claim 16 wherein the formulation is administered with a polymer concentration below the critical gel concentration of the polymer under isotonic conditions and a temperature between room temperature and body temperature.

19. The method of claim 16 comprising applying the formulation to the site at a polymer concentration less than the critical gel concentration of the polymer, wherein water is absorbed from the formulation to the site to increase the concentration of the polymer to form a barrier.

20. The formulation of claim 7, wherein the abnormal proliferation is cancer or endometriosis.

\* \* \* \* \*